United States Patent [19]
Brierley et al.

[11] Patent Number: 5,116,324
[45] Date of Patent: May 26, 1992

[54] PROTECTOR FOR IV SITE

[76] Inventors: Carol L. Brierley, 2512 S. Rennington; Lisa Wolf, 1718 S. Lingmore #55, both of Mesa, Ariz. 85202

[21] Appl. No.: 730,087
[22] Filed: Jul. 15, 1991
[51] Int. Cl.⁵ .............................. A61M 5/32
[52] U.S. Cl. ...................... 604/180; 604/174; 128/DIG. 6
[58] Field of Search ............ 604/174, 179, 180; 128/DIG. 26, DIG. 6, 877, 887, 888

[56] References Cited

U.S. PATENT DOCUMENTS

| | | | |
|---|---|---|---|
| 3,900,026 | 8/1975 | Wagner | 604/174 |
| 4,059,105 | 11/1977 | Cutruzzula et al. | 604/180 |
| 4,517,971 | 5/1985 | Sorbonne | 128/DIG. 6 |
| 4,583,977 | 4/1986 | Shishov et al. | 604/174 |
| 4,626,246 | 12/1986 | Verkade | 604/174 |
| 4,659,329 | 4/1987 | Annis | 604/180 |
| 4,679,553 | 7/1987 | Proulx et al. | 604/174 |
| 4,767,405 | 8/1988 | Lokken | 604/180 |
| 4,846,807 | 7/1989 | Safadago | 604/179 |

Primary Examiner—Cary E. O'Connor
Attorney, Agent, or Firm—Gregory J. Nelson

[57] ABSTRACT

A protector for a venepuncture site having a flexible base with peripherally extending taping tabs for adhesively securing the protector about the venepuncture site. An openable transparent shield or cover is hinged to the base to provide acces to the site. The opposite ends of the base form openings or bridge sections which allow IV tubing to pass between the base and the patient. The cover is provided with aperture to access tubing for temporary or short time infusions.

12 Claims, 1 Drawing Sheet

PROTECTOR FOR IV SITE

BACKGROUND OF THE INVENTION

Field of the Invention

The present invention relates to the field of intravenous catheters and more particularly relates to a protector which protects the venepuncture site, catheter, attached intravenous tubing and injection cap.

Intravenous catheters are extensively used for hydration and the administration of medications, feeding and for blood transfusions. Representative intravenous fluids include medications of various types, blood, plasma, dextrose, and saline solutions. IV infusions are generally carried out with a container of IV fluid suspended above the patient and the fluid is delivered to the patient at an administration needle or catheter through a drip chamber and flexible tubing connected to the container at a piercing spike. The infusion flow rate is regulated by use of an external pinch valve, in-line controller or IV pump. Medication may also be administered by direct injection.

Initially when infusions are carried out, the tubing and catheter are purged of air by initiating a flow of fluid through the tubing. The catheter is then inserted into a vein at a suitable location such as in the wrist area and the infusion is initiated. Preferably when the venepuncture site (sometimes venipuncture) is located at or adjacent a joint, the area should be properly stabilized. The appropriate flow rate is established by timing the rate of flow at the drip chamber.

When intravenous fluid is to be administered to a patient over an extended period of time, it is general practice to insert the catheter into the venepuncture site and retain the catheter in position by an adhesive membrane such as that commonly known as Opsite. This simple arrangement helps to protect the venepuncture site and stabilization of the catheter, however, this procedure does not protect the exposed portion of the catheter and tubing. Accordingly, it is easy for a patient to inadvertently strike a portion of the bed or engage the bed clothes with the catheter or tubing which will cause movement of the catheter at the venepuncture site. This occurrence may cause pain to the patient and more importantly may result in deterioration of the venepuncture site so that the readministration of the IV will be required which involves substantial time on the part of the medical attendant. The medical regulations of most states require that IV's be administered only by physicians or registered nurses so the professional medical time involved in repeating these procedures as well as additional supplies requested for a re-start and represent added expense to the hospital and patient. Re-starts also take the physician or nurse away from other important duties. Trauma at the venepuncture site increases the chances for infection and increases the risk of phlebitis.

The problems due to an exposed catheter are particularly acute today since conventional medical practice often requires leaving the catheter in place after completion of the intravenous infusion. The exposed end of the catheter is capped with an injection cap (sometimes termed a Heparin Lock) to provide convenient access for the administration of medications such as emergency drugs, antibiotics, diuretics and cortico steroids.

In addition to the problem of inadvertent contact of the IV catheter and associated tubing, some patients present particular problems. Pediatric patients may be especially active and curious and may through such activity dislodge the catheter. Similarly, some patients due to medications, emotional, physical or psychological condition may intentionally interfere with medical equipment and procedures including the catheter.

Because of the concern of medical personnel relative to protection of the vena site, medical personnel have often resorted to make-shift devices to enclose the site. One common method involves the use of a portion of an expanded foam or acrylic drinking cup which has been longitudinally cut in half. Generally the cup half is inverted and placed over the area and taped in place. Obviously there are substantial disadvantages with make-shift devices of this type in that it may present sharp edges, is hard to secure in place and is unduly bulky. Such an arrangement has an unprofessional appearance which may be of medical concern to the patient. These types of make-shift devices may not be transparent or may obstruct visualization of the IV site so that the device must be removed to inspect the site.

Because of the problems of patient vena site protection discussed above and a general dissatisfaction with make-shift measures, there are a number of venepuncture shields found in the prior art including the following:

U.S. Pat. No. 3,722,508 shows a combined infusion guard and immobilizer having a portion conforming to a limb such as an elbow, wrist or ankle. Velcro-type hook and eye straps are employed for fastening the immobilizer to a limb or extremity. The infusion guard has an arch extending from one side of the immobilizer to the other side which are connected by complimentary connectors along the length of the immobilizer and guard. The guard includes means for clamping an intravenous tube to the guard and an opening for passing a protecting loop of tubing between the clamp and the intravenous needle.

U.S. Pat. No. 4,919,150 discloses an intravenous catheter shield formed by a base underlying a portion of the patient's limb. A transparent, channel-like housing is hinged to the base and overlies the catheter area in vertical spaced relationship. Velcro-type straps secure the patient's limb to the base and the outer surface of the housing is provided with resilient clamps which grip an IV tube extending across the housing and into the housing interior.

U.S. Pat. No. 4,870,976 shows an injection shield assembly made of rigid transparent plastic material. The assembly includes strap members for holding the assembly to a limb. The assembly when positioned on the limb is longitudinally extending with respect to the limb. A space is defined between the upper most surface of the shield and the limb. Intravenous tubing and a needle can be positioned in this space.

U.S. Pat. No. 4,846,807 shows an IV tube anchor and shield. The device has a continuous frame of resilient foam material strapped to the patient with a central aperture of the frame surrounding the puncture area. A separate dome with ventilation apertures is attachable over the central aperture of the frame to shield the needle. The IV tube is anchored to the frame at a plurality of different locations. The IV tube is threaded through a slot and under tabs in the frame to return bent, or preferably serpentine path and is maintained in position by straps which also secure the frame and dome combination to the body.

While the above devices represent an improvement over the make-shift devices often used for protecting the IV site, these prior art devices have certain disadvantages. Many of the prior art devices, specifically for this purpose, are cumbersome, awkward, and are unnecessarily large and difficult to use. Further, may of the devices are cost prohibitive in today's cost conscious medical industry. The use or incorporation of limb restraints and Velcro-type fasteners adds to the cost and complexity of the devices. Strap-type devices may restrict circulation requiring additional nursing time in circulation checking and documentation. Strap-type devices can act as a tourniquet in the event of IV infiltration and have the additional disadvantage of not being easily useable with injection caps.

Therefore, the principal object of the present invention is to provide a device for shielding and protecting an IV site to minimize the possibility of painful and potentially harmful contact of the IV needle or attached tubing to nearby objects.

Another object of the present invention is to provide a device which is simple, compact and inexpensive to manufacture and which is disposable and is reliable and effective for shielding the IV site.

Another object of the present invention is to provide an IV site protector with a transparent, openable cover for inspection and attendance to the IV site.

Another object of the present invention is to provide an IV site protector having a flexible base which may be placed at various locations and positions on the patient's anatomy and secured by adhesive tape, which tape may be selected to be compatible with the patient such as a hypo-allergenic tape.

Another object of the present invention is to provide an IV protector which is symmetrically configured so it can be conveniently placed in various positions on the patient's body.

Another important object of the present invention is to provide an IV venepuncture protector which may be used to protect a catheter attached to an IV needle or to an unattached IV catheter equipped with an injection cap.

Briefly, the present invention provides a device for protecting and shielding an IV site which device includes a flexible base member fabricated from an elastomeric material. The base member is symmetrical having a plurality of peripherally projecting taping tabs so that the base may be easily secured to the patient at the IV site by use of suitable adhesive medical tape such as Micropore tape. The tabs are optimally located to provide tape securement locations to facilitate placement at various positions on the body of the patient. The opposite ends of the base are formed having openings or recesses permitting IV tubing to pass beneath or through the ends of the device. The tape tabs are configured having retention features to better engage the tape.

A transparent or semi-transparent shield member is secured to the protector base at a living hinge. The base and shield may be integrally formed or the shield may be a thermoplastic material which is secured to the hinge by an appropriate fastener or adhesive member. In the closed position, the shield and base are provided with complimentary locking features which secure the shield in place over the venepuncture site. The nurse or medical attendant may unlock the shield and base, pivoting the shield to an open position for access to the site without disturbing the base. The shield defines oppositely disposed openings so the nurse can open the shield, attach a short-time IV infusion (i.e. antibiotic), close the shield with the attached tubing extending between the cover and base. The base does not have to be removed or disturbed with this procedure.

The above and other objects and advantages of the present invention will become more apparent from the following description and claims taken in conjunction with the accompanying drawings in which:

Figure 1:
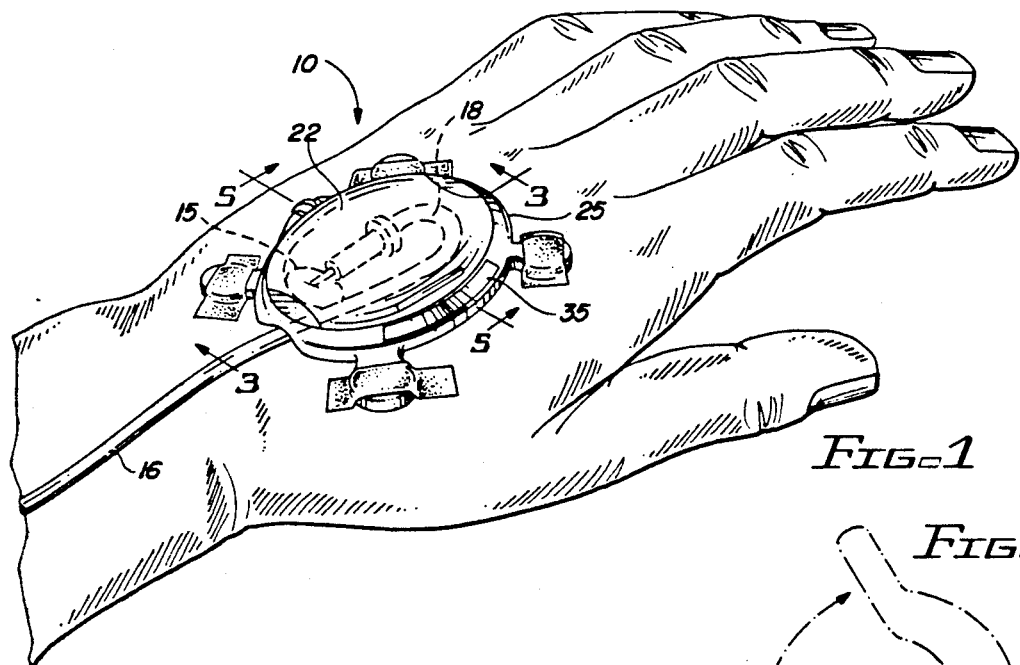
FIG. 1 is a perspective view of an IV protector in accordance with the present invention shown in position in an IV site at the back of the hand of a patient.

FIG. 1 illustrates the IV protector of the present invention which is generally designated by the numeral 10. The protector 10 is shown in position at an IV site in the back of the hand of the user which is a common location for the administration of IV's. The IV set includes an administration catheter 12 which has been inserted into the vena system of the patient. The catheter terminates at a connector 14 which during the administration of the IV is attached to an IV tubing line 16. As is conventional, the IV tubing line is generally reversely looped at 18 to stabilize the catheter. The IV tubing is connected to a suitable source of IV fluid across a drip chamber and appropriate flow rate control device which are not shown as these are conventional and form no part of the invention. It is common medical practice to leave the catheter in position after the administration of the IV. In this case, the IV tubing is disconnected from the catheter and an injection cap is placed over the connector 14. The cap generally includes a membrane through which medication, antibiotics or other fluids can easily be injected into the venous system of the patient. As will be more apparent from the discussion which follows, the protector of the present invention shields the IV catheter and a portion of the attached tubing during administration of the IV and also will serve to protect the catheter and injection cap when the catheter remains in place after the administration of the IV. As is normal, a patch of clear plastic film or membrane 15 often termed "Opsite" is shown as in position and adhesively secured to the patient's skin at the venepuncture site.

It will also be appreciated that while the present invention has been described for use in connection with the administration of IV's, the shield may be used with various types of probes or catheters which may be inserted to the blood system or body of the patient. For example, the protector may be used with both intravenous probes and arterial catheters and may also be used to protect devices such as drainage tubes which may be inserted into an incision or surgical location and connected to a tube to drain fluid from these locations.

Figure 4:
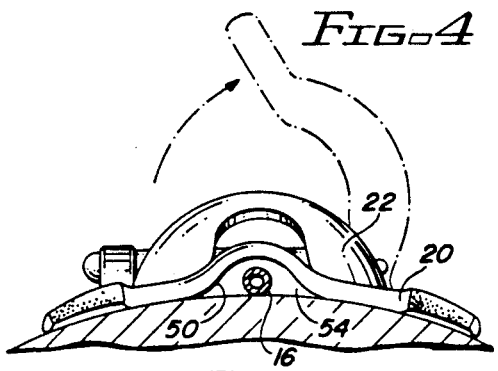
FIG. 4 is an end view of the IV protector of the present invention shown in an open position.
Figure 3:
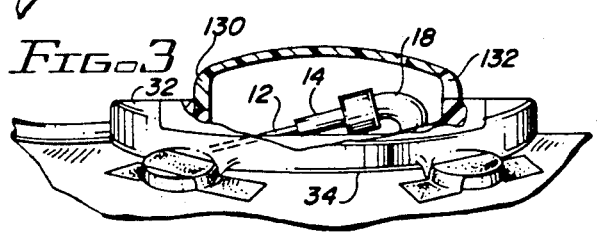
FIG. 3 is a sectional view of the IV protector of the present invention taken along line 3—3 of FIG. 1.
Figure 5:
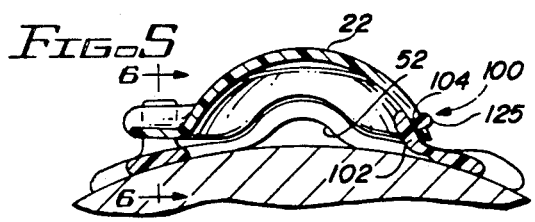
FIG. 5 is a sectional view taken along line 5—5 of FIG. 1.
Figure 2:
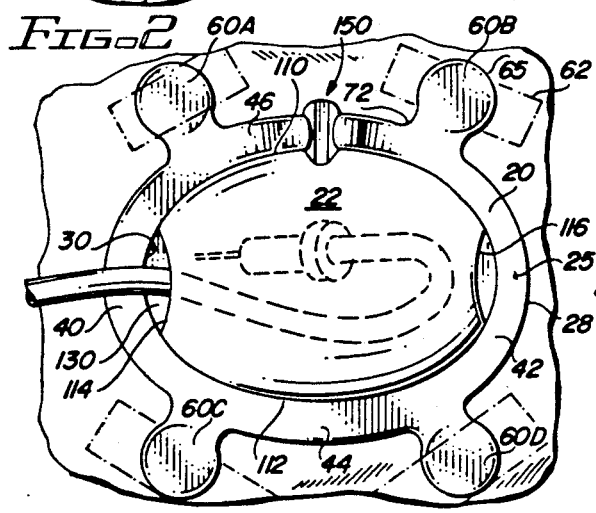
FIG. 2 is a top plan view of the IV protector of the present invention showing a short-time IV infusion set-up.

The protector 10 of the present invention consists of a base 20 and a cover 22 which is hinged to the base. The base, as shown in FIGS. 1 and 2, has a generally oval or elliptical body member or rim 25. The rim 25 has an outer edge 28, an inner edge 30, top 32 and bottom surface 34. As best seen in FIGS. 4 and 5, the bottom surface is transversely curved. As indicated in the top view, FIG. 2, the overall configuration of the device is preferably symmetrical with respect to both the longitudinal and transverse axis so that the device is reversible and may be adapted to various locations on the patient's anatomy. For purposes of reference, the opposite portions 40 and 42 will be referred as the ends of the shield and rim portions 44, 46 will be designated the sides of the base of the shield. The term "longitudinal" refers to central axis extending end-to-end and "transverse" refers to a central axis extending across the sides of the device.

The rim at opposite ends 40, 42 is configured having elevated, U-shaped bridge sections 50, 52, respectively, located at an intermediate location preferably centered with respect to the longitudinal axis of the base. The bridge members 50, 52 each define an area 54 beneath the bridge which when the device is in position on the patient will permit the passage of one or preferably two side-by-side segments of IV tubing to the interior of the protector as seen in FIG. 4.

Figure 8A:
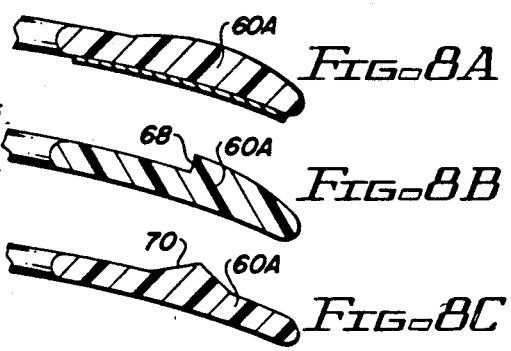
FIGS. 8A to 8C illustrate alternate cross-sectional configurations for the tape retention tabs.
Figure 8B:
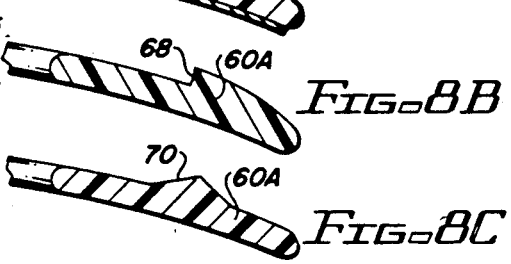
Figure 8C:

A plurality of projections 60A, 60B, 60C and 60D, extend generally radially outwardly from the base 25. The projections serve to provide an easily accessible surface over which strips 62 of medical adhesive tape may be placed to secure the protector in place. Projections 60A, 60B are shown spaced apart along side 46 each approximately 45° from the transverse axis. Similarly, projections 60C, 60D are spaced apart on side 44 of the rim, each approximately 45° from the transverse axis. The projections may have various configurations as viewed from the top and may be rectangular but are preferably shown as having a somewhat circular outer edge 65 which eliminates any sharp edges or projections. Further, as best seen in FIG. 8A which shows tab 60A which is representative, the upper surface of the projection is slightly domed or convex to provide better tape retention. Other topological configurations may be provided for tape retention. For example, the projections may be configured as shown in FIG. 8B in which a shoulder 68 is defined by an edge extending diametrically across the surface of the projection. Alternately, as shown in FIG. 8C, a generally conical projection 70 may be formed on the upper surface of the tab or projection. The projections are shown having a reduced area neck 72 at the point of attachment to the rim which provides improved flexibility. Although a plurality of projections are preferred, a continuous flange-type projection could also be used.

A label strip 35 is provided on the rim 25 at a convenient location as shown in FIG. 1. The label strip may be a slightly roughened area or an adhesive member which will accept a writing material such as ink to allow a nurse to indicate information concerning the IV such as date, time, medication and identification of the responsible nurse or doctor.

Part of a locking device or fastener is integrally formed at an intermediate location at side 46. The locking device consists of a pair of spaced apart posts 80, 82 which will frictionally engage a portion of the protector as will be explained hereafter with reference to the cover.

The base may be formed from a wide variety of medically acceptable materials. The device is intended for single patient use and preferably is a product formed from natural rubber, latex, silastic or any number of medical-grade elastomeric materials which can be molded. The elastomeric qualities of the base help to make the device compatible with various venepuncture locations and anatomical requirements of the patient.

As best seen in FIG. 5, the longitudinally extending portion of the inner edge 30 of side 44 is provided with a thin hinge section 100 having a tab 102 which connects to the shield cover 22. Preferably the hinge section 100 is integrally formed with the base and is of reduced thickness forming a "living hinge".

The shield cover 22 is generally in the form of a dome curving both longitudinally and transversely. The cover is preferably transparent or at least semi-transparent and has opposite side edges 110 and 112 and opposite ends 114 and 116. A slot 104 extends longitudinally adjacent edge 112 and receives projecting post 125 so as to secure the cover or dome to the base at the hinge 100. The edges 110, 112 of the cover are configured to rest on or closely conform to the corresponding, adjacent inner edges of the base. The cover is formed of a hard, clear thermoplastic material such as a medical-grade acrylic. The opposite ends 114, 116 of the cover extend transversely between the sides spaced inwardly from the inner edge 30 of the base defining spaces 130, 132 respectively at either end of the cover. These spaces serve several functions both allowing ventilation to the protected area around the venepuncture site and allow space for temporary IV tubing to pass through.

Figure 6:
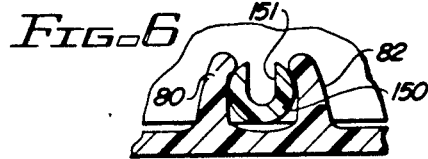
FIG. 6 is an enlarged sectional view of the lock as indicated by line 6—6 in FIG. 5.
Figure 7:
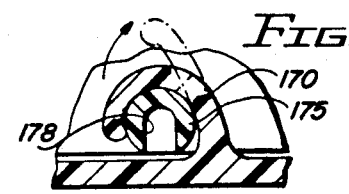
FIG. 7 is a view similar to FIG. 6 showing an alternate embodiment of the lock.

Latch member 150 extends laterally from the edge of the cover and is formed integrally therewith. As best seen in FIGS. 6 and 7, the latch member 150 has a generally cylindrical configuration with a U-shaped channel 151 extending longitudinally therein. The latch is frictionally received between the upstanding posts 80, 82 of the base to retain the cover in a locked position on the base. In order to facilitate engagement and disengagement of the lock, some flexibility is provided in the post members 80, 82. The degree of frictional resistance as well as the length of the latch extending beyond the posts 80, 82 are selected so as to require a predetermined minimum amount of force and dexterity to open the cover. This design will minimize the possibility of the cover being inadvertently opened during use due to accidental engagement of the latch on an object as well as discouraging intentional opening of the device by a patient, particularly a pediatric or confused patient.

FIG. 7 shows an optional configuration for the latch between the cover and base. In this embodiment, the latch is again is shown as a generally cylindrical member 175 having a channel-shaped recess 178 defined therein. A flexible upstanding post 170 is integrally formed with the base which has a downwardly turned distal end. The end of the post may be manually deflected upwardly as shown in dotted lines to permit the latch to be engaged and thereafter released allowing the post to return to the latched condition. This latch design tends to minimize the possibility of the cover being inadvertently unlatched and also requires some degree of dexterity and strength to reduce the chance of the cover being opened by a patient such as a smaller child. The latch design is more easily opened with two hands which deters patients from opening the protectors.

In the preferred embodiment, the IV protector of the present invention is intended for single patient use and should be discarded after use. The dimensions of the IV shield may vary but for most adults would generally be approximately three inches in length and approximately three inches in width. However, for pediatric use and some specialized uses, the device may be made smaller or larger, as required, and preferably, the various sizes may be indicated by appropriate color coding. For example, the color of the device intended for normal adult use might have a blue base whereas pediatric sizes might typically be provided with a base of another color such as yellow. This color coding will facilitate the selection of the proper shield for the application, particularly in emergency situations.

The IV protector of the present invention will be better understood from the following description of use. Medical personnel will initially establish the IV. The laws of most states require that either a doctor or a registered nurse start the IV. The IV site is selected and the catheter is connected to a source of IV fluid by flexible tubing across a drip chamber which permits the drop rate to be visually determined. The flow rate is controlled either by an external roller clamp, in-line IV control valve or IV pump. Once the catheter is connected to the source of fluid and the fluid generally suspended from the stand, the system is purged of air and thereafter the catheter is inserted into a convenient vein which often is in the back of the hand as shown in FIG. 1. The area immediately adjacent the venepuncture site is generally covered by a thin film or membrane 15 having adhesive surface which is sometimes termed op site. The attached tubing is generally reversely looped at 18 as shown in FIG. 1 and the tubing extended along the arm of the patient. In order to protect the venepuncture site and the adjacent area, the IV protector 10 of the present invention is positioned about the venepuncture site once the IV is running. The device is centered about the venepuncture site generally with the base positioned in a manner which best conforms to the anatomy of the patient. The transversely curved surface of the base will conform comfortably to the curve of the back of the hand and wrist area as well as most any other location where a suitable vein is located. Clearance area for the tube is provided at base 20 at area 54 allowing the IV tube 16 to easily pass beneath the base without any restriction imposed on the tubing. Once the protector is in place, it is manually held in position and strips of adhesive tape 62 of suitable length are placed over the projections 60A, 60B, 60C and 60D and onto the patient's skin. The type of tape can be selected in accordance with the patient's medical requirements. Tape such as Micropore tape can be used but other types of tapes are also suitable in the case of a patient with allergies or if other special medical conditions exist. Normally the shield is positioned with the hinged side of the dome adjacent the patient and the clasp or lock laterally positioned on the patient.

The cover 22 is closed by engaging the latch 150 in the cooperating lock members 80, 82. The cover protects the IV site, catheter and any associated tubing from various conditions that may be harmful to the patient. The cover is generally elliptical and provides a smooth exterior, thus, if it comes in contact with an object there are no corners to catch on the object. The protector protects the area enclosed within the protector in the event the patient's arm or hand strikes an object such as a portion of the bed. The protector also protects the catheter and associated tubing at the venepuncture site from becoming engaged on bed clothes which can cause the needle to become dislodged or loosened which may increase risk of infection. The transparent cover allows medical personnel to periodically visually inspect the IV site. The openings in the cover permit adequate ventilation to the site. The tubing loop and tubing extending beneath the base of the IV shield is protected and stabilized.

As indicated, it is common medical practice to leave the capped IV needle in position after the IV administration has been terminated. The IV needle provides a convenient site for administration of medications which can be conveniently accomplished by inserting a syringe into the membrane in the injection cap after opening the protector cover. Temporary IV infusions can be established without removing the base by lifting the cover and extending the tubing between the cover and base as shown in FIG. 2.

In the event the IV is terminated, the tubing can be disconnected from the catheter and a suitable cap placed on the needle. Access to the catheter is provided by lifting the hinged cover. It is noted that the operation of the clasp on the hinged cover requires at least a minimal degree of dexterity and strength which serves to minimize or prevent the possibility of the cover from being accidentally or intentionally opened by a patient such as a small child.

The taping projections 60A, 60B, 60C and 60D provide convenient locations for securement of the protector to the patient and in various orientations and positions. This feature provides a significant advantage over shields using Velcro-type straps which extend about a limb. Straps or bands which extend around the limb of a patient can easily cut-off circulation resulting in a tourniquet effect. Many hospitals have strict policies prohibiting use of any device that may restrict circulation. Also, it is not uncommon for IV's to infiltrate with fluid escaping into surrounding tissue instead of into the vein. This situation can cause a limb to swell rapidly which may result in a dangerous situation with devices which have a tourniquet affect.

With the present invention, the IV site is protected and reduces the necessity of having to re-start the IV in the event the IV site becomes damaged and unsuitable for the IV as a result of impact or interference with the a nearby object. The cost to a patient and to the hospital in having to re-start an IV can be significant and will also occupy the valuable time of medical personnel. Further, re-starting of an IV is uncomfortable and even painful for the patient as well as increasing the risk of infection.

The locking arrangement of the device is simple and provides some resistance to inadvertent opening or tampering by the patient.

The cover being transparent allows the nurse or medical personnel to observe the venepuncture site to look for bleeding or other abnormality. Since the venepuncture site is protected, the likelihood of trauma is reduced as well as the occurrence of attendant conditions such as infection, phlebitis and the like. It is also important to note that the tubing extending from the IV catheter is not attached to the cover or other component of the protector but simply passes beneath the rim or peripheral flange of the base so that in the event the protector is struck against an object such as a bed frame, the blow should not dislodge the IV catheter.

As indicated above, the device can be provided in various sizes for adult and pediatric uses and may be suitably color coded for convenience of selection. The device is intended for single patient use and intended for disposal after such use. Preferably, the device is fabricated from suitable medical-grade plastics with the components preferably being molded. However, it is possible that the device can be integrally formed from a single material such as a clear elastomeric or thermoplastic with the living hinge and latch integrally formed at the same time.

It will be obvious to those skilled in the art to make various changes, alterations and modifications to the invention described herein. It is to be understood that such changes, alterations and modifications are intended to be encompassed within the scope of the appended claims.

We claim:

1. A protective shield to be positioned at a location on the human body about a venepuncture site, said shield comprising:
   (a) a flexible base having a bottom surface defining an opening to be placed about the site;
   (b) a protective cover openably attached to said base and extending at least partially across said opening, said cover having a first open position permitting access to the site and a closed position in which the shield extends at least partially across the opening;
   (c) a projection extending from said base having a surface for attachment of an adhesive member to secure said shield with said adhesive member to the body at the said site; and
   (d) wherein the exterior surface of said cover is generally dome-shaped and in a closed position defines an aperture providing access to the venepuncture site.

2. The shield of claim 1 wherein said cover is openably attached to said base at a hinge.

3. The shield of claim 1 wherein said cover is fabricated from a relatively rigid transparent plastic material.

4. The shield of claim 1 wherein said projection comprises a plurality of tabs extending therefrom and wherein said tabs are symmetrical with respect to said base.

5. The shield of claim 4 wherein said tabs are provided with a tape retention feature.

6. The shield of claim 1 wherein said cover and said base are provided with cooperable fastener members for selectively maintaining said cover in said closed position.

7. The shield of claim 1 wherein said bottom surface of said base is generally transversely curved and further wherein said base defines a raised bridge portion to accommodate the passage of tubing between the base and the body of the patient.

8. The shield of claim 1 wherein said base is provided with an identification strip for receipt of IV related information.

9. A protective shield to be placed on a patient's body about an IV site comprising:
   (a) a flexible generally oval annular base having a bottom surface which is generally transversely curved, said base having a first fastener member at one location and a hinge member at an opposite location thereon, a portion of the base defining a bridge to permit the passage of IV tubing between the base and patient's body;
   (b) a plurality of flexible tape tabs projecting from said base at opposite generally symmetrical locations, said tape tabs having an upper surface provided with a tape retention feature; and
   (c) a generally smooth cover formed of a transparent plastic material, said cover being secured to said hinge member at one side and having a second fastener member cooperative with said first fastener member to selectively secure said cover in a closed position, said cover defining an edge spaced from said base in a closed position of the cover to provide access to the IV site.

10. The shield of claim 9 wherein said shield is provided in multiple sizes and each of said sizes is coded.

11. The shield of claim 10 wherein said coding is color coding.

12. The shield of claim 9 further including an identification strip for receipt of IV related information.

* * * * *